United States Patent [19]

Carlsson et al.

[11] Patent Number: 4,613,695
[45] Date of Patent: Sep. 23, 1986

[54] N-NITROSO COMPOUNDS AND COMPOSITIONS CONTAINING SUCH COMPOUNDS

[75] Inventors: Jan-Inge L. Carlsson; Herta G. Jensen Petersen; Anders R. Stamvik, all of Helsingborg, Sweden

[73] Assignee: Aktiebolaget Leo, Helsingborg, Sweden

[21] Appl. No.: 529,718

[22] Filed: Sep. 6, 1983

[30] Foreign Application Priority Data

Sep. 17, 1982 [SE] Sweden ............................ 8205324

[51] Int. Cl.$^4$ ................... C07C 143/76; C07C 143/74; A61K 31/445; A61K 31/18
[52] U.S. Cl. ..................................... 564/33; 546/231; 546/247; 548/569
[58] Field of Search ................. 564/33; 546/231, 247; 548/569; 424/321, 267, 322, 224; 514/359, 331, 315, 428, 318, 422, 603, 605, 601

[56] References Cited

PUBLICATIONS

Physicians' Desk Reference, vol. 38, 1984, p. 735.
National Cancer Institute Monograph for Mar. 1977, pp. 43, 75–80, 81–92.

Primary Examiner—Charles F. Warren
Assistant Examiner—Carolyn S. Greason
Attorney, Agent, or Firm—Gordon W. Hueschen

[57] ABSTRACT

The invention concerns N-nitroso compounds having the general formula:

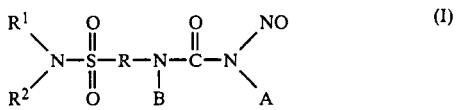

wherein

A is lower alkyl or halolower alkyl;

B is hydrogen; lower alkenyl; lower alkynyl; 3–6 C cycloalkyl; —RSO$_2$NR$^3$R$^4$, or lower alkyl optionally monosubstituted with lower alkoxy, or 3–6 C cycloalkyl;

R is straight or branched 2–5 C alkylene, optionally monosubstituted with SO$_2$NR$^3$R$^4$ or CONR$^3$R$^4$, said alkylene always containing at least two carbon atoms separating the nitrogen atom of the urea from any SO$_2$NR$^1$R$^2$ or SO$_2$NR$^3$R$^4$;

R$^1$ and R$^2$ are the same or different and selected from hydrogen, 5–6 C cycloalkyl, lower alkoxy, phenyl, benzyl, and straight or branched 1–6 C alkyl, optionally monosubstituted with hydroxy, lower alkoxy, SO$_2$NR$^3$R$^4$, or CONR$^3$R$^4$; R$^1$ and R$^2$ may also together form a 4–5 C alkylene; and R$^3$ and R$^4$ are the same or different and selected from hydrogen or lower alkyl, or R$^3$ and R$^4$ together are a 4–5 C alkylene, together with pharmaceutical compositions thereof; processes for their manufacture, and methods of treatment.

The compounds of formula (I) have antitumor activity.

12 Claims, No Drawings

N-NITROSO COMPOUNDS AND COMPOSITIONS CONTAINING SUCH COMPOUNDS

This invention relates to aminosulfonylalkyl nitrosoureas having an antitumor activity and to the preparation thereof. The invention is also concerned with pharmaceutical compositions containing said compounds and methods of treatment therewith.

BACKGROUND OF THE INVENTION

Specific 1-(2-chloroethyl)-1-nitrosoureas, e.g. carmustine (BCNU; 1,2-bis-(2-chloroethyl)-nitrosourea), lomustine (CCNU; 1-(2-chloroethyl)-3-cyclohexyl-1-nitrosourea) and semustine (Methyl-CCNU; 1-(2-chloroethyl)-3-(4-methyl-cyclohexyl)-1-nitrosourea) are used as chemotherapeutic agents for the treatment of a number of experimental and clinical tumours (1).

It is generally known, however, that these compounds have several serious toxic effects, e.g. damaging effects on liver, kidney, lung organs, and also bone marrow depression, neurotoxicity and gastrointestinal toxicity (1–4).

One new compound of the same type, chlorozotocin or 2-/3-(2-chloroethyl)-3-nitrosoureido/-D-glucopyranose, which is under clinical evaluation, has been shown to possess decreased bone marrow toxicity (5), but the other types of toxicities are still evident, e.g. liver and lung toxicity (6, 7).

It is also generally known that after some time tumours tend to develop resistance to the anticancer therapy employed, thus rendering the therapy without curative effect.

Thus, the need exists for new and improved chemotherapeutic agents of this type, either or both with increased antitumour activity and decreased toxicity.

GENERAL DESCRIPTION OF THE INVENTION

It has now, surprisingly, been found that the novel aminosulfonyl nitrosoureas of the present invention corresponding to the general formula (I) as defined below, possess improved chemotherapeutic properties in comparison with several known and clinically used nitrosourea antitumour agents. Thus, the compounds of the invention show improved therapeutic indexes and good oral cytostatic activity against the Walker 256 carcinosarcoma and the L1210 lymphatic leukemia. The new compounds also possess a greater ameliorative or curative potential as shown by the L1210 experimental results.

The compounds can be used as such or combined with either solid or liquid carriers or diluents and made available in varying amounts in such pharmaceutical forms as e.g., tablets, pills, capsules, pellets, powders, ointments, suppositories and aqueous or non-aqueous suspensions and solutions.

OBJECTS OF THE INVENTION

Accordingly, one object of the invention is to provide new compounds of the general formula (1), having the aforesaid activity, together with a relatively low degree of toxicity.

A second object is to provide such type of compounds, which can be employed in disorders responsive to treatment with anticancer agents and with immunosuppressive agents for the amelioration or palliation thereof.

Another object of the invention is to provide processes for preparing the new compounds having the general formula (I).

Yet another object of the invention is to provide compositions containing as an active ingredient one or more of the compounds, having the general formula (I), preferably together with a pharmaceutically acceptable carrier and, if desired, other pharmacologically active agents.

Other objects of the invention will be apparent to one skilled in the art, and still other objects will become apparent hereinafter.

SUMMARY OF THE INVENTION

According to the invention there are provided compounds having the general formula:

$$\begin{array}{c} R^1 \\ \diagdown \\ R^2 \diagup \end{array} N - \underset{\underset{O}{\overset{O}{\|}}}{S} - R - \underset{B}{N} - \overset{O}{\overset{\|}{C}} - N \begin{array}{c} \diagup NO \\ \diagdown A \end{array} \qquad (I)$$

wherein A is lower alkyl or halolower alkyl; B is hydrogen, lower alkenyl, lower alkynyl, 3–6 C cycloalkyl, $-RSO_2NR^3R^4$, or lower alkyl optionally monosubstituted with lower alkoxy, or 3–6 C cycloalkyl; R is straight or branched 2–5 C alkylene, optionally monosubstituted with $SO_2NR^3R^4$ or $CONR^3R^4$, said alkylene always containing at least two carbon atoms separating the N of the urea from any $SO_2NR^1R^2$ or $SO_2NR^3R^4$; $R^1$ and $R^2$ are the same or different and selected from hydrogen, 5–6 C cycloalkyl, lower alkoxy, phenyl, benzyl, lower alkyl, and straight or branched 1–6 C alkyl, optionally monosubstituted with hydroxy, lower alkoxy, $SO_2NR^3R^4$, or $CONR^3R^4$; $R^1$ and $R^2$ may also together form a 4–5 C alkylene; $R^3$ and $R^4$ are the same or different and selected from hydrogen or lower alkyl, $R^3$ and $R^4$ may also together form a 4–5 C alkylene.

In this disclosure the expression "lower" means that the group referred to contains 1–4 C (C=carbon) atoms, inclusive. Thus, lower alkyl, lower alkenyl, lower alkynyl and lower alkoxy include for instance: methyl, ethyl, propyl, isopropyl, butyl, secondary butyl, isobutyl, tertiary butyl, allyl, propargyl, methoxy, ethoxy, propoxy, isopropoxy, butoxy, isobutoxy, secondary butoxy and tertiary butoxy.

Furthermore the expression "halo" means fluorine, chlorine, bromine or iodine.

As regards the substituent A, it is preferred that this substituent is 2-chloroethyl or 2-fluoroethyl, especially 2-chloroethyl.

Also, as regards the substituent B, it is preferred that this substituent is hydrogen or lower alkyl, especially hydrogen.

Furthermore, such compounds are preferred wherein R is unsubstituted straight 2–5 C alkylene or wherein R is ethylene, especially unsubstituted ethylene.

Especially preferred compounds are such wherein one of the substituents $R^1$ and $R^2$ is methyl and the other is lower alkyl or 2-hydroxyethyl, or wherein $R^1$ and $R^2$ are the same and are hydrogen, methyl, ethyl, or propyl, or wherein $R^1$ and $R^2$ together are 5 C alkylene.

Most preferred compounds are such wherein $R^1$ and $R^2$ are hydrogen and/or methyl.

The following compounds are preferred:
(a) 1-(2-chloroethyl)-3-/2-(dimethylaminosulfonyl)ethyl/-1-nitrosourea (b) 1-(2-chloroethyl)-3-/2-(diethylaminosulfonyl)ethyl/-1-nitrosourea
(c) 3-/2-(aminosulfonyl)ethyl/-1-(2-chloroethyl)-1-nitrosourea
(d) 1-(2-chloroethyl)-1-nitroso-3-/2-(1-piperidinosulfonyl)ethyl/-urea
(e) 1-(2-chloroethyl)-3-/2-(methylaminosulfonyl)ethyl/-1-nitrosourea
(f) 1-(2-chloroethyl)-3-/2-(dipropylaminosulfonyl)ethyl/-1-nitrosourea
(g) 1-(2-chloroethyl)-3-/2-(2-hydroxyethylaminosulfonyl)ethyl/-1-nitrosourea
(h) 1-(2-chloroethyl)-3-/2-(N-2-hydroxyethyl-N-methyl-aminosulfonyl)ethyl/-1-nitrosourea
(i) 1-(2-chloroethyl)-3-(2-/2-methoxyethylaminosulfonyl/ethyl)-1-nitrosourea
(j) 1-(2-chloroethyl)-3-/2-(dimethylaminosulfonyl)ethyl/-3-methyl-1-nitrosourea
(k) 1-(2-chloroethyl)-3-(5-/dimethylaminosulfonyl/pentyl)-1-nitrosourea
(l) 1-(2-chloroethyl)-3-(3-/dimethylaminosulfonyl/propyl)-1-nitrosourea
(m) 1-(2-chloroethyl)-3-(4-/dimethylaminosulfonyl/butyl)-1-nitrosourea
(n) 1-(2-chloroethyl)-3-(2-/N-ethyl-N-propylaminosulfonyl/ethyl)-1-nitrosourea

METHODS OF PREPARATION

The compounds having the general formula (I) may be prepared by conventional methods.

A general process (Method 1 below) for preparing compounds having the general formula (I) is as follows:

Method 1

Compounds of the general formula (I) are prepared by N-nitrosation of a corresponding urea having the general formula

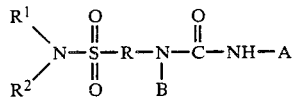 (II)

wherein $R^1$, $R^2$, R, B and A are as defined above.

Among other methods for preparing compounds having the general formula (I) the following may be mentioned:

Method 2

An amine having the general formula

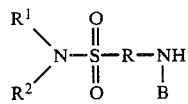 (III)

wherein $R^1$, $R^2$, R and B are as defined above, is reacted with an N-alkyl-N-nitroso-carbamoyl derivative of the general formula

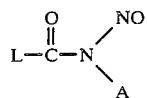 (IV)

wherein A is as defined before, and wherein L is a suitable leaving group.

Methods 1 and 2 are illustrated by the following processes:

A. A process according to Method 1, characterized by reacting a urea (II) with a nitrosating agent. Several different such agents are known and the following may be mentioned: Metal nitrites, such as alkali metal nitrites, e.g., sodium, potassium and lithium nitrite, in combination with an acid, e.g. hydrochloric acid, acetic acid, formic acid and methane sulfonic acid; nitrosyl chloride (NOCl); dinitrogen trioxide ($N_2O_3$); dinitrogen tetroxide ($N_2O_4$); mixtures of various nitrogen oxides; nitrosyl sulfuric acid ($HO_3S$-ONO); nitrosonium tetrafluoroborate ($NOBF_4$); alkyl nitrites, e.g. propyl nitrite and isoamyl nitrite; and nitric acid in combination with a suitable reducing agent, e.g., copper dust.

Although the process may be performed at ambient temperatures, normally subambient temperatures such as around 0° C. and sometimes even substantially lower, e.g., around −60° C., are employed, thus to prevent thermal degradation of the compounds of the general formula (I). Normally, temperatures of −10° to +25° C., inclusive, are suitable. Also protection from light is advantageous to prevent the corresponding photolytic degradation.

The process may be carried out in an inert solvent medium which, depending on the choice of nitrosating agent, may be a chlorinated hydrocarbon, e.g., carbon tetrachloride, methylene chloride, chloroform; dimethyl formamide, acetic anhydride, pyridine, an alcohol, e.g., ethanol, water; and in nitrosation with a metal nitrite the acid used in this conjunction may also function as the solvent medium, either alone or in a mixture with the above inert solvent medium. Mixtures of more than one solvent may also be employed.

Some nitrosating agents, e.g., nitrosyl chloride, dinitrogen tetroxide and nitrosylsulphuric acid, release a strong acid in the reaction with a urea (II), and in such cases a suitable base, e.g., potassium acetate, may be used in the process to neutralize such formed strong acid. This may similarly also be accomplished by using e.g., pyridine as both solvent and base.

Nitrosation of a urea (II) with an alkyl nitrite is performed in the presence of a suitable nucleophilic anionic catalyst, e.g., chloride or isothiocyanate anions.

Some of the foregoing methods for preparation of compounds of the general formula (I) are summarized in reference (10).

Method 1 above is further illustrated in Examples 1-3, inclusive.

B. A process according to Method 2, characterized by reacting an amine (III) with an N-alkyl-N-nitroso carbamoyl derivative (IV), wherein the group L of (IV) is a suitable leaving group.

Among such leaving groups, L, the following may be mentioned: Azido ($N_3-$); substituted phenoxy, i.e. ortho- or para-nitrophenoxy, ortho- or para-cyanophenoxy, polyhalophenoxy such as 2,4,5-trichloro-, pentachloro-, or pentafluorophenoxy; and 1-(2,5-pyrrolidinedione)oxy-.

Although the process may be performed at ambient temperatures, subambient temperatures, such as around 0° C., may be employed and may also be advantageous to prevent thermal degradation of the compounds of the general formulas (I) and (IV). Normally, temperatures of −10° to +25° C., inclusive, are suitable. Also, protection from light is advantageous to prevent the corresponding photolytic degradation.

Suitable inert solvents which may be employed in the process are, e.g., dimethyl formamide, chlorinated hydrocarbons such as methylene chloride, alcohols such as methanol, ethanol, n- and iso-propanol, and pyridine.

Some of the foregoing procedures for preparation of compounds of the general formula (I) are given in reference (11) and references given therein.

Method 2 above is further illustrated in Examples 4–8, inclusive.

METHODS OF PREPARATION OF INTERMEDIATES (a) The compounds of the general formula (II), which are useful in Method 1 above as starting materials for the preparation of the compounds of the general formula (1) are prepared by known methods, for example methods a-1 and a-2 below:

(a-1) A compound of the general formula (III) is reacted with an alkyl isocyanate to give a compound of the general formula (II), e.g. according to reference (12). This method is further illustrated in Example 17.

(a-2) A compound of the general formula (III) is reacted with phosgene to give the corresponding isocyanate or carbamoyl chloride (e.g. according to reference /18/), followed by reaction with a primary amine as in the above method to give a compound of the general formula (II).

This two step procedure is further illustrated in Example 18.

(b) The compounds of the general formula (III), which are useful as starting materials in Method 2 above for the preparation of the compounds of the general formula (I), are prepared by known methods, for example methods b-1, b-2, b-3 and b-4 below:

(b-1) An aminoalkylsulfonic acid having the general formula

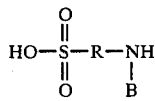
(V)

wherein R and B are as defined above, is converted to its N-protected derivative, e.g. the N-phthaloyl derivative (B=hydrogen), the N-benzyloxycarboxyl derivative, or the N-/2,2,2-trichloroethoxycarbonyl/derivative, converted with phosphorous pentachloride to the corresponding chlorosulfonylderivative, reacted with an amine of the general formula

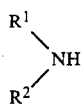
(VI)

wherein $R^1$ and $R^2$ are as defined above, and the N-protecting group is removed to give a compound of the general formula (III), e.g. according to reference (19) and (20).

This method is further illustrated in Example 19.

(b-2) A bis(aminoalkyl)disulfide having the general formula

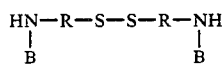
(VII)

wherein R and B are as defined above, is converted to its N-protected derivative, e.g. the N-phthaloyl derivative (B=hydrogen), the N-benzyloxycarbonyl derivative, or the N-/2,2,2-trichloroethoxycarbonyl/derivative, oxidized e.g. with chlorine to the corresponding chlorosulfonylderivative, reacted with an amine of the general formula

(VI)

wherein $R^1$ and $R^2$ are as defined above, and the N-protecting group is removed to give a compound of the general formula (III), e.g. according to reference (21).

(b-3) A dihaloalkene, e.g. a dibromoalkene having the general formula

(VII)

wherein R has the same meaning as defined above, is reacted with phthalimidoalkyl to a bromoalkylphthalimide, then reacted with thiourea to a S-phthalimidoalkyl thiouronium bromide, oxidized with e.g. chlorine to a phthalimidoalkylsulfonyl chloride, reacted with an amine of the general formula

(VI)

wherein $R^1$ and $R^2$ are as defined above, and the phthalimido group removed to give a compound of the general formula (III), e.g. according to reference (22).

This method is further illustrated in Example 20.

(b-4) Other routes for the preparation of compounds of the general formula (III) are also known, as described e.g. in reference (9).

(c) The compounds of the general formula (IV), which are useful in Method 2 above as starting materials for the preparation of the compounds of the general formula (I) are prepared by known methods, e.g. according to references (10), (11), (12) and references given therein.

In synthesizing the compounds having the general formulas (II), (III) and (IV), each group of compounds involved must be compatible with the process in question or, if necessary, protected during one or more reaction steps and then converted to the desired group. Pertinent examples of groups that may be protected are hydroxy, carboxyl, sulfonic acid, primary or secondary amino groups. Examples of such protecting groups are found in, e.g., references (13, 14, 15).

Pharmaceutical formulations are usually prepared from a predetermined quantity of one or more of the compounds of the invention. Such formulations may take the form of powders, syrups, suppositories, ointments, solutions, pills capsules, pellets or tablets, suspensions, emulsions, oil solutions, etc, with or without, but preferably with, any one of a large variety of pharmaceutically acceptable vehicles or carriers. When in a mixture with a pharmaceutical vehicle or carrier, the active ingredient usually comprises from about 0.01 to 75 percent, normally from about 0.05 to about 15 percent, by weight of the composition. Carriers such as cellulose, sugar, talc, commonly used synthetic and natural gums, water, and the like, may be used in such formulations. Binders such as polyvinylpyrrolidone and lubricants such as sodium stearate, may be used to form tablets. Disintegrating agents such as starch may also be included in tablets.

DETAILED DESCRIPTION OF THE INVENTION

The following examples are intended to illustrate but not to limit the scope of the invention, although the compounds named are of particular interest for our intended purposes. These compounds have been designated by underlined numbers in the examples where their systematic names are given. The compounds are later referred to by a number code, a:b, where a means the number of the example wherein the preparation of the compound in question is described, and b refers to the order of the compounds prepared according to that example. Thus, compound 1:2 means the second compound prepared according to Example 1.

The structures of the compounds found in Examples 1–12 are confirmed by NMR and elementary analysis. The NMR data are obtained using a 60 MHz instrument (Perkin Elmer R 12).

EXAMPLE 1

1-(2-chloroethyl)-3-/2-(dimethylaminosulfonyl)ethyl/urea (54.2 g, 0.02 mol) is dissolved in a mixture of glacial acetic acid (20 ml) and acetic anhydride (100 ml). The solution is cooled to 0° C. and sodium nitrite (27.6 g, 0.4 mol) is added while stirring over a period of 2 hours. The reaction mixture is maintained at 0° C. for 10 hours and then added to a mixture of ice and water. The reaction product is extracted with ether, which is then washed with water, 5% aqueous sodium carbonate solution, and water. After drying over anhydrous sodium sulphate, the ether is evaporated in vacuo.

The product, 1-(2-chloroethyl)-3-/2-(dimethylaminosulfonyl)ethyl/-1-nitrosourea (1), is isolated and purified by preparative HPLC, is pure by TLC and has a melting point of 65°–67.5° C.

In essentially the same manner the following compounds are obtained from the corresponding starting materials.

2. 1-(2-chloroethyl)-3-(2-/diethylaminosulfonyl/ethyl)-1-nitrosourea, m. p. 68° C.
3. 3-(2-/aminosulfonyl/ethyl)-1-(2-chloroethyl)-1-nitrosourea, m. p. 115°–118° C.
4. 1-(2-chloroethyl)-1-nitroso-3-(2-/1-piperidinosulfonyl/ethyl)-urea, m. p. 83° C.
5. 1-(2-chloroethyl)-3-(2-/methylaminosulfonyl/ethyl)-1-nitrosourea, m. p. 84°–86° C.
6. 1-(2-chloroethyl)-3-(2-/dipropylaminosulfonyl/ethyl)-1-nitrosourea, m. p. 69° C.
7. 3-(2-/benzylaminosulfonyl/ethyl)-1-(2-chloroethyl)-1-nitrosourea, m. p. 76°–78° C.
8. 1-(2-chloroethyl)-3-(2-/2-methoxyethylaminosulfonyl/ethyl)-1-nitrosourea, m. p. about 15° C.
9. 3-(2-/butylaminosulfonyl/ethyl)-1-(2-chloroethyl)-1-nitrosourea, m. p. 55°–56° C.
10. 3-(2-/t-butylaminosulfonyl/ethyl)-1-(2-chloroethyl)-1-nitrosourea
11. 1-(2-chloroethyl)-3-(2-/cyclohexylaminosulfonyl/ethyl)-1-nitrosourea, m. p. 85°–87° C.
12. 3-(2-/bis(2-hydroxyethyl)aminosulfonyl/ethyl)-1-(2-chloroethyl)-1-nitrosourea
13. 1-(2-chloroethyl)-3-(2-/1-methylpentylaminosulfonyl/ethyl)-1nitrosourea, m. p. 24°–26° C.
14. 1-(2-chloroethyl)-3-(2-/2-hydroxyethylaminosulfonyl/ethyl)-1-nitrosourea
15. 1-(2-chloroethyl)-3-(2-/N-2-hydroxyethyl-N-methyl-aminosulfonyl/ethyl)-1-nitrosourea, m. p. about 15° C.
16. 1-(2-chloroethyl)-3-(2-/1,1-dimethyl-2-hydroxyethylaminosulfonyl/ethyl)-1-nitrosourea
17. 3-(2-/N-benzyl-N-methylaminosulfonyl/ethyl)-1-(2-chloroethyl)-1-nitrosourea, m. p. 74°–75° C.
18. 1-(2-chloroethyl)-3-(2-/N-methyl-N-phenylaminosulfonyl/ethyl)-1-nitrosourea, m. p. 83° C.
19. 1-(2-chloroethyl)-3-(5-/dimethylaminosulfonyl/pentyl)-1-nitrosourea, m. p. 59°–60° C.
20. 1-(2-chloroethyl)-3-(2-/N-methoxy-N-methylaminosulfonyl/ethyl)-1-nitrosourea, m. p. 55° C.
21. 1-(2-chloroethyl)-3-(3-/dimethylaminosulfonyl/propyl)-1-nitrosourea, m. p. 99° C.
22. 1-(2-chloroethyl)-3-(2-/4-methylbenzylaminosulfonyl/ethyl)-1-nitrosourea, m. p. 70° C.
23. 1-(2-chloroethyl)-3-(2-/2-(dimethylaminosulfonyl)ethylaminosulfonyl/ethyl)-1-nitrosourea, m. p. 70°–72° C.
24. 1-(2-chloroethyl)-3-(4-/dimethylaminosulfonyl/butyl)-1-nitrosourea, m. p. 83° C.
25. 3-(2-/dimethylaminosulfonyl/ethyl)-1-(2-fluoroethyl)-1-nitrosourea
26. 3-(2-/dimethylaminosulfonyl/ethyl)-1-methyl-1-nitrosourea
27. 1-(2-bromoethyl)-3-(2-/dimethylaminosulfonyl/ethyl)-1-nitrosourea
28. 1-(2-chloroethyl)-3-(2-/N-cyclohexyl-N-methylaminosulfonyl/ethyl)-1-nitrosourea
29. 1-(2-chloroethyl)-3-(2-/cyclopentylaminosulfonyl/ethyl)-1-nitrosourea
30. 3-(2-/2-(aminosulfonyl)ethylaminosulfonyl/ethyl)-1-(2-chloroethyl)-nitrosourea
31. 1-(2-chloroethyl)-3-(2-/2-(methylaminosulfonyl)ethylaminosulfonyl/ethyl)-1-nitrosourea
32. 3-(2-/2-(aminocarbonyl)ethylaminosulfonyl/ethyl)-1-(2-chloroethyl)-1-nitrosourea
33. 1-(2-chloroethyl)-3-(2-/2-(methylaminocarbonyl)ethylaminosulfonyl/ethyl)-1-nitrosourea
34. 1-(2-chloroethyl)-3-(2-/2-(dimethylaminocarbonyl)ethylaminosulfonyl/ethyl)-1-nitrosourea
35. 1-(2-chloroethyl)-3-(1-/dimethylaminocarbonyl/-2-/dimethylaminosulfonyl/ethyl)-1-nitrosourea
36. 1-(2-chloroethyl)-3-(2-/dimethylaminosulfonyl/propyl)-1-nitrosourea
37. 3-(bis-2,3/dimethylaminosulfonyl/propyl)-1-(2-chloroethyl)-1-nitrosourea
38. 3-(bis-1,3-/dimethylaminosulfonyl/propan-2-yl)-1-(2-chloroethyl)-1-nitrosourea
39. 1-(2-chloroethyl)-3-(1-/dimethylaminocarbonyl/-3-/dimethylaminosulfonyl/-propan-2-yl)-1-nitrosourea
40. 1-(2-chloroethyl)-3-(1-/dimethylaminosulfonyl/-2-methylpropan-2-yl)-1-nitrosourea
41. 1-(2-chloroethyl)-3-(1-/dimethylaminosulfonyl/propan-2-yl)-1-nitrosourea
42. 1-(2-chloroethyl)-3-(1-/dimethylaminosulfonyl/butan-2-yl)-1-nitrosourea
43. 3-(bis-1,3-/aminosulfonyl/propan-2-yl)-1-(2-chloroethyl)-1-nitrosourea
44. 3-(1-/aminocarbonyl/-2-/aminosulfonyl/ethyl)-1-(2-chloroethyl)-1-nitrosourea 45. 1-(2-chloroethyl)-3-(2-/dimethylaminosulfonyl/ethyl)-3-methyl-1-nitrosourea
46. 3-allyl-1-(2-chloroethyl)-3-/2-(dimethylaminosulfonyl)ethyl/-1-nitrosourea
47. 1-(2-chloroethyl)-3-propargyl-3-/2-(dimethylaminosulfonyl)ethyl/-1-nitrosourea
48. 1-(2-chloroethyl)-3-(2-methoxyethyl)-3-/2-(dimethylaminosulfonyl)ethyl/-1-nitrosourea
49. 1-(2-chloroethyl)-3-cyclohexyl-3-/2-(dimethylaminosulfonyl)ethyl/-1-nitrosourea
50. 1-(2-chloroethyl)-3-cyclopropylmethyl-3-/2-(dimethylaminosulfonyl)ethyl/-1-nitrosourea
51. 3,3-bis-/2-(dimethylaminosulfonyl)ethyl/-1-nitrosourea
52. 1-(2-chloroethyl)-3-(2-/N-ethyl-N-methylaminosulfonyl/ethyl)-1-nitrosourea, m. p. ~25° C.
53. 1-(2-chloroethyl)-3-(2-/N-ethyl-N-propylaminosulfonyl/ethyl)-1-nitrosourea, m. p.~20° C.
54. 1-(2-chloroethyl)-3-(2-/dimethylaminosulfonyl/ethyl)-3-ethyl-1-nitrosourea.

EXAMPLE 2

To a cooled (−60° C.) solution of dinitrogen tetroxide (4.14 g, 0.045 mol) in glacial acetic acid (50 ml) anhydrous sodium acetate (7.38 g, 0.09 mol) is added. The temperature is raised to 0° C., and 1-(2-chloroethyl)-3-(2-/dimethylaminosulfonyl/ethyl)urea (7.73 g, 0.03 mol) is added while stirring. After continued stirring at 0° C. for 30 minutes the mixture is added to a mix of ice and water. The reaction product is extracted with ether, which is then washed with water, 5% aqueous sodium carbonate solution, and water. After drying over anhydrous sodium sulphate the ether is evaporated in vacuo. The product, 1-(2-chloroethyl)-3-(2-/dimethylaminosulfonyl/ethyl)-1-nitrosourea (the same compound as 1:1), is isolated and purified by preparative HPLC, is pure by TLC and has a melting point of 65°–67.5° C.

EXAMPLE 3

1-(2-chloroethyl)-3-(2-/dimethylaminosulfonyl/ethyl)urea (5.16 g, 0.02 mol) is dissolved in a mixture of glacial acetic acid (100 ml) and acetic anhydride (40 ml), and freshly fused potassium acetate (16 g) and phosphorus pentoxide (4 g) is added. The resulting mixture is cooled to +5° C., and a solution of nitrosyl chloride (5 g) in acetic anhydride (25 ml) is added dropwise while stirring. After the addition, stirring is continued for 2 hours at +10° C. The reaction mixture is added to a mix of ice and water, and the reaction product is extracted with diethyl ether which is then washed with water, 5% aqueous sodium carbonate solution and water. After drying over anhydrous sodium sulphate the diethyl ether is evaporated in vacuo. The product, 1-(2-chloroethyl)-3-(2-/dimethylaminosulfonyl/ethyl)-1-nitrosourea (the same compound as 1:1), is isolated and purified by preparative HPLC, is pure by TLC, and has a melting point of 65°–67.5° C.

EXAMPLE 4

A solution of 2-amino-N,N-dimethyl-ethanesulfonamide hydrochloride (4.72, 0.025 mol) in abs. ethanol (30 ml) is cooled to 0° C. Triethyl amine (3.5 ml) is added and the mixture is added dropwise to a solution of N-(2-chloroethyl)-N-nitroso carbamoyl azide (5.4 g, 0.03 mol). The reaction mixture is stirred for 2 hours at 0° C. and is then evaporated to dryness in vacuo. Diethyl ether is added to the residue, and the precipitated triethyl amine hydrochloride is filtered off. The diethyl ether solution is evaporated in vacuo to dryness. The product, 1-(2-chloroethyl)-3-(2-/dimethylaminosulfonyl/ethyl)-1-nitrosourea (the same compound as 1:1), is isolated and purified by preparative HPLC, is pure by TLC and has a melting point of 65°–67.5° C.

In essentially the same manner compounds 1:2 to 1:44, inclusive, and 1:54 are obtained from the corresponding starting materials.

EXAMPLE 5

To a solution of 2-amino-N,N-dimethyl-ethanesulfonamide hydrochloride (5 g, 0.026 mol) in methanol (60 ml) is added triethyl amine (2.68 g). The mixture is stirred for 10 minutes, and p-nitrophenyl N-(2-chloroethyl)-N-nitroso carbamate (7.25 g, 0.026 mol) is added. After stirring at room temperature for 2 hours the mixture is evaporated in vacuo to dryness, and methylene chloride (50 ml) and triethyl amine (10 ml) is added. The resulting solution is washed twice with water (50 ml), twice with 2 M hydrochloric acid (40 ml), and with water. After drying over anhydrous sodium sulphate the solution is evaporated to dryness in vacuo. The product, 1-(2-chloroethyl)-3-(2-/dimethylaminosulfonyl/ethyl)-1-nitrosourea (the same compound as 1:1), is isolated and purified by preparative HPLC, is pure by TLC and has a melting point of 65°–75.5° C.

In essentially the same manner compounds 1:2 to 1:44, inclusive, and 1:54 are obtained from the corresponding starting materials.

1-(2-chloroethyl)-3-(2-/dimethylaminosulfonyl/ethyl)-1-nitrosourea (the same compound as 1:1) is also prepared essentially in the same manner from the same above mentioned amine and o-nitrophenyl N-(2-chloroethyl)-N-nitroso carbamate or o-cyanophenyl N-(2-chloroethyl)-N-nitroso carbamate.

EXAMPLE 6

To a solution of 2-aminoethanesulfonamide hydrochloride (5 g, 0.030 mol) in methanol (70 ml) triethylamine (3.13 g) is added. The mixture is stirred for 10 minutes and p-nitrophenyl N-(2-chloroethyl)-N-nitroso carbamate (8.75 g, 0.032 mol) is added. After stirring at room temperature for 2 hours the mixture is evaporated in vacuo to dryness, and the residue is extracted with methylene chloride (30 ml). The undissolved crystalline material is filtered off and washed with methylene chloride. The product obtained, 3-(2-/aminosulfonyl/ethyl)-1-(2-chloroethyl)-1-nitrosourea (the same compound as 1:3), is pure in TLC without further chromatographic purification and is dried in vacuo over phosphorus pentoxide. The melting point of the product obtained is 115°–118° C.

EXAMPLE 7

To a solution of 2-amino-N,N-dimethyl-ethanesulfonamide hydrochloride (5 g, 0.026 mol) in methanol (60 ml) triethyl amine (2.68 g) is added. The mixture is stirred for 10 minutes and 1-/N-(2-chloroethyl)N-nitrosoaminocarbonyloxy/-2,5-pyrrolidine-dione (6.94 g, 0.028 mol) is added. After stirring at room temperature for 2 hours the reaction mixture is evaporated in vacuo to dryness and the residue is dissolved in methylene chloride. The solution is washed with water (4×50 ml) and dried over sodium sulphate. After filtration the dry solution is evaporated in vacuo to dryness. The product, 1-(2-chloroethyl)-3-(2-/dimethylaminosulfonyl/ethyl)-1-nitrosourea (the same compound as 1:1), is isolated and purified by preparative HPLC, is pure in TLC and has a melting point of 65°–67.5° C.

EXAMPLE 8

To a solution of 2-aminoethanesulfonamide hydrochloride (5 g, 0.030 mol) in methanol (70 ml) triethyl amine (3.13 g) is added. The mixture is stirred for 10 minutes and p-cyanophenyl-N-(2-chloroethyl)-N-nitroso carbamate (8.11 g, 0.032 mol) is added. After stirring at room temperature for 3 hours the reaction mixture is evaporated in vacuo to dryness and the residue is extracted with cold methylene chloride. The undissolved crystalline material is filtered off and washed with cold methylene chloride. The product obtained, 3-(2-/aminosulfonyl/ethyl)-1-(2-chloroethyl)-1-nitrosourea (the same compound as 1:3), is pure in TLC without further chromatographic purification, and is dried in vacuo over phosphorus pentoxide. The melting point of the product obtained is 115°–118° C.

EXAMPLE 9

This example illustrates the effect of compounds of the present invention in inhibiting the growth of several tumours. From the results obtained it is obvious that the compounds of the present invention have improved toxicological and therapeutic properties, resulting in increased therapeutic indexes, in comparison with commercially available antitumour agents.

A therapeutic index is an indication of the therapeutic usefulness of a compound, and such an index may be defined in various ways. One type of therapeutic index commonly used is the ratio LD50/ED50, wherein LD50 is the dose that causes a 50 percent lethality, and ED50 is the dose that causes a 50 percent reduction of tumour size. Another type of therapeutic index, useful in evaluation of increasing survival time, is the ratio between maximum and minimum effective dose. Both these types of therapeutic indexes are used and given in the experimental results below.

The experimental design and interpretation of the results are in accordance with the standards set by the CCNSC (see reference (16)) and by the DR&D (see reference (17)).

The manner of administration of the compounds is by the oral (p. o.) route in each case.

Some of the results obtained are given in Tables 1–2.3 below.

This example shows that the new compounds are useful to prevent the growth of tumours and can therefore be employed in treating a living animal body suffering from disorders responsive to treatment with anticancer agents and immunosuppresive agents.

Walker carcinosarcoma 256

Experimental animals: Female Sprague Dawley rats
Tumour implants: Tumour pieces with 2–3 mm diameter, implanted subcutaneously
Therapy: The compound is administered p. o. once on the day after the implantation
Termination: The animals are killed on the 9th day after implantation
Evaluation: Weight of tumour is determined in test animals and compared with those of control animals. For each compound the LD50 and ED50 dose (as defined above) are determined. The therapeutic index, T. I., (LD50/ED50) is calculated.

TABLE 1
ANTITUMOUR RESULTS ON WALKER CARCINOSARCOMA 256

| Compound | LD50 mg/kg | ED50 mg/kg | T.I. LD50/ED50 |
|---|---|---|---|
| BCNU | 50 | 1 | 50 |
| CCNU | 90 | 1 | 90 |
| Cyclophosphamide | 180 | 6 | 30 |
| 1:1 | 50 | 0.25 | 200 |
| 1:2 | 60 | 0.4 | 150 |
| 1:3 | 40 | 0.2 | 200 |
| 1:4 | 125 | 1 | 125 |
| 1:5 | 40 | 0.25 | 160 |
| 1:6 | 250 | 2 | 125 |
| 1:7 | 250 | 2 | 125 |
| 1:14 | 90 | 0.6 | 150 |
| 1:15 | 90 | 0.6 | 150 |
| 1:19 | 250 | 1 | 250 |
| 1:24 | 250 | 2 | 125 |
| 1:28 | >250 | 2.5 | >100 |
| 1:53 | 250 | 1.7 | 147 |

In preliminary experiments the following additional compounds are found to exhibit significant activity in the foregoing test in a dose of 8 mg/kg: 18 to 1:13, inclusive; 1:16 to 1:18, inclusive; 1:20 to 1:23, inclusive; 125 to 1:45, inclusive; 1:48, 1:52 and 1:54.

Lymphatic leukemia L1210

Experimental animals: Female $BDF_1$ mice
Tumour implants: $10^5$ tumour cells implanted intraperitoneally (i. p.)
Therapy: The compounds were administered p. o. once on the day following the implantation.
Termination: The animals were killed on the 60th day after the implantation. Living animals on the 60th day are termed long term survivors.
Evaluation:
(a) Evaluation of therapeutic dose range for survival time increase: Survival times at various dose levels are determined, and the survival time of the test animals (t) is expressed as the percentage of that of the control animals (c):

t·100/c (%)

The maximum effective dose and the minimum effective dose required to achieve t·100/c≧125% are determined, and a therapeutic index as defined below is calculated:

T. I.$_s$=max.effect.dose/min.effect.dose.

Some of the results obtained are shown in Table 2:1.
(b) Evaluation of therapeutic dose range for long term survival: Long time survival is determined at various dose levels and is expressed as surviving test animals on day 60 (T) as the percentage of that of the total number of test animals ($T_o$):

T·100/$T_o$(%)

The maximum effective dose and the minimum effective dose to achieve long term survival T·100/$T_o$>20% are determined and a therapeutic index, T. I.$_{ls}$ is calculated:

T. I.$_{ls}$=max.effect.dose/min.effect.dose.

Some of the results obtained are shown in Table 2:2.

(c) Evaluation of cure potential: The normal survival time for test animals receiving no therapeutic treatment is 9–11 days. Surviving test animals on the 60th day after implantation showing no sign of tumour presence are regarded as cured animals. Long term survival is determined as under (b) above, and the effective dose or dose range to achieve a long term survival $T \cdot 100/T_o \geq 90\%$ is determined as an evaluation of the cure potential. Some of the results obtained are shown in Table 2:3.

TABLE 2:1
EVALUATION OF THERAPEUTIC RANGE FOR SURVIVAL TIME INCREASE

| Compound | Maximum effective dose$^{(x)}$ mg/kg | Minimum effective dose$^{(x)}$ mg/kg | T.I.s Max. eff. dose / Min. eff. dose |
|---|---|---|---|
| BCNU | 63 | 16 | 4 |
| Methyl-CCNU | 31 | 8 | 4 |
| 1:1 | 63 | 8 | 8 |
| 1:2 | 125 | 16 | 8 |
| 1:4 | 125 | 8 | 16 |
| 1:5 | 63 | 8 | 8 |
| 1:6 | 250 | 31 | 8 |
| 1:9 | 125 | 16 | 8 |
| 1:11 | 250 | 31 | 8 |
| 1:14 | 125 | 16 | 8 |
| 1:15 | 125 | 16 | 8 |
| 1:17 | 500 | 63 | 8 |
| 1:20 | 125 | 16 | 8 |
| 1:21 | 63 | 8 | 8 |
| 1:24 | 250 | 31 | 8 |
| 1:28 | 250 | 31 | 8 |
| 1:53 | 500 | 31 | 16 |

$^{(x)}$Median survival time percent of control $\geq 125\%$

The following additional compounds are found to exhibit significant activity (i.e. median survival time percent of control $\geq 125\%$) in a dose of 125 mg/kg in the foregoing test: 1:10; 1:13; 1:18; 1:25–1:27, inclusive; 1:29–1:45, inclusive; and 1:54.

TABLE 2:2
EVALUATION OF THERAPEUTIC RANGE FOR LONG TERM SURVIVAL

| Compound | Maximum effective dose$^{(x)}$ mg/kg | Minimum effective dose$^{(x)}$ mg/kg | T.I.s Max. eff. dose / Min. eff. dose |
|---|---|---|---|
| BCNU | 63 | 63 | 1 |
| Methyl CCNU | none | none | none |
| Chlorozotocin | " | " | " |
| 1:1 | 63 | 31 | 2 |
| 1:2 | 125 | 63 | 2 |
| 1:3 | 31 | 16 | 2 |
| 1:4 | 125 | 31 | 4 |
| 1:7 | 250 | 125 | 2 |
| 1:8 | 63 | 31 | 2 |
| 1:9 | 125 | 63 | 2 |
| 1:11 | 125 | 63 | 2 |
| 1:14 | 125 | 31 | 4 |
| 1:15 | 125 | 31 | 4 |
| 1:17 | 250 | 125 | 2 |
| 1:19 | 125 | 63 | 2 |
| 1:20 | 125 | 63 | 2 |
| 1:21 | 63 | 31 | 2 |
| 1:23 | 125 | 63 | 2 |
| 1:24 | 250 | 63 | 4 |
| 1:28 | 250 | 125 | 2 |
| 1:52 | 63 | 31 | 2 |

TABLE 2:2-continued
EVALUATION OF THERAPEUTIC RANGE FOR LONG TERM SURVIVAL

| Compound | Maximum effective dose$^{(x)}$ mg/kg | Minimum effective dose$^{(x)}$ mg/kg | T.I.s Max. eff. dose / Min. eff. dose |
|---|---|---|---|
| 1:53 | 250 | 125 | 2 |

$^{(x)}$Dose levels to achieve >20% long term survivors, i.e. test animal survivors on day 60.

TABLE 2:3
EVALUATION OF CURE POTENTIAL

| Compound | Dose or dose range for cure$^{(x)}$ mg/kg |
|---|---|
| BCNU | none |
| Methyl CCNU | " |
| Chlorozotocin | " |
| 1:1 | 31–63 |
| 1:4 | 125 |
| 1:5 | 31 |
| 1:6 | 125 |
| 1:8 | 31–63 |
| 1:9 | 63 |
| 1:11 | 125 |
| 1:12 | 125 |
| 1:14 | 63 |
| 1:15 | 63 |
| 1:16 | 250 |
| 1:19 | 125 |
| 1:20 | 63–125 |
| 1:21 | 31–63 |
| 1:23 | 125 |
| 1:24 | 125 |
| 1:28 | 125 |
| 1:53 | 125–150 |

$^{(x)}$Cure defined as test with $\geq 90\%$ long term survivors, i.e. test animal survivors on day 60.

EXAMPLE 10

Manufacturing process for tablets à 20 mg

| Model batch of 1000 tablets | | |
|---|---|---|
| I | Solid Active Compound, mesh$^{(+)}$ 70 | 20 g |
| | Lactosum, Ph.Nord. | 210 g |
| | Amylum maidis, Ph.Nord. | 75 g |
| | Kollidon 25, B.A.S.F. | 3.5 g |
| II | Aqua purificata | q.s. |
| III | Talcum, Ph.Nord. | 15 g |
| | Magnesii stearas, Ph.Nord. | 1.5 g |
| Weight of 1000 tablets | | 325 g |
| Weight of 1 tablet: 325 mg | | |

$^{(+)}$The mesh standard is according to the international system of code DIN 4189/1968.

Punch: 10.5 Mix mm round, flat, scored, bevel-edged

Mix the screened substances I thoroughly and then moisten with II, whereupon the mixture is granulated through a stainless sieve no 10 (mesh 25). Dry the granulate in an oven at a maximum temperature of 25° C., then repeat sieving through sieve no 10. Add the substances under III and mix thoroughly. Punch tablets with a gross weight of about 325 mg.

EXAMPLE 11

Suspension for injection 20 mg/ml

| Active Compound, mesh 100 | 20 mg |
|---|---|
| Sodium chloride | 8 mg |
| Carboxy methylcellulose | 1 mg |
| Benzyl alcohol | 1 mg |

EXAMPLE 12

Oral suspension 5 mg/ml

| Active Compound, mesh 100 | 5 mg |
|---|---|
| Sorbitol | 600 mg |
| Flavouring compound | q.s. |
| Colour | q.s. |
| Water to make | 1 ml |

EXAMPLE 13

Suppositoria à 25 mg

| Active Compound | 25 mg |
|---|---|
| Cocoa butter | q.s. |

EXAMPLE 14

Ointment 2%

| Active Compound | 2 g |
|---|---|
| Triethanolamine | 1 g |
| Glycerol | 7 g |
| Cetanol | 2.5 g |
| Lanoline | 2.5 g |
| Stearic acid | 20 g |
| Sorbitan monooleate | 0.5 g |
| Sodium hydroxide | 0.2 g |
| Methyl paraben | 0.3 g |
| Propyl paraben | 0.1 g |
| Ethanol | 0.9 g |
| Water to make | 100 g |

EXAMPLE 15

Capsules à 10 mg

| Active Compound | 10 mg |
|---|---|
| Magnesium stearate | 2 mg |
| Talcum | 188 mg |

The substances are mixed and filled into capsules

EXAMPLE 16

10 mg sterile powder to be dissolved in water for injection

| Water-soluble Active Compound | 10 mg |
|---|---|
| Sodium chloride | 4 mg |
| Methyl paraben | 0.7 mg |
| Propyl paraben | 0.3 mg |

The substances are dissolved in distilled water
The solution is dispensed in vials and freeze-dried

PREPARATION OF INTERMEDIATES (examples 17–20)

EXAMPLE 17

2-amino-N,N-dimethylethanesulfonamide hydrochloride (5.64 g, 0.03 mol) is dissolved in chloroform (50 ml) while adding triethylamine (4.7 ml). The solution is cooled to 0° C. and a mixture of 2-chloroethyl isocyanate (2.83 ml, 0.04 mol) and chloroform (25 ml) is added dropwise. The reaction mixture is stirred for 4 hours at room temperature and washed with water (3×50 ml). The organic phase is dried over anhydrous sodium sulphate, filtered and evaporated in vacuo to dryness. The product obtained is 1-(2-chloroethyl)-3-(2-/dimethylaminosulfonyl/ethyl)-urea, m. p. 126° C.

In essentially the same manner other compounds of the general formula (II) above are obtained from the corresponding compounds of the general formula (III) by reaction with the corresponding isocyanate.

EXAMPLE 18

2-amino-N,N-dimethylethanesulfonamide (4.72 g, 0.025 mol) is dissolved in chloroform (50 ml) while adding triethyl amine (3.8 ml, 0.027 mol). The solution is cooled to 0° C. and triethyl amine (3.8 ml, 0.027 mol) is added. A solution of phosgene (3 g, 0.03 mol) in chloroform (25 ml) is added dropwise while stirring. The reaction mixture is stirred for about 1 hour. A solution of 2-fluoroethyl amine hydrochloride (3.0 g, 0.03 mol) and triethyl amine (4 ml, 0.03 mol) in chloroform (50 ml) is added dropwise while stirring and cooling. The reaction mixture is stirred at room temperature for 1 hour and then washed with 0.1 M hydrochloric acid (50 ml) and water (2×50 ml). The organic phase is dried and evaporated in vacuo to dryness. The product obtained is 3-(2-/dime- thylaminosulfonyl/ethyl)-1-(2-fluoroethyl)-urea.

In essentially the same manner the following compound is obtained from the corresponding starting materials.

2. 1-(2-bromoethyl)-3-(2-/dimethylaminosulfonyl/ethyl)-urea.

EXAMPLE 19

A mixture of taurine (100 g, 0,8 mol), potassium acetate (83,8 g, 1.4 mol) and glacial acetic acid (283 ml) is boiled under stirring and reflux for 10 minutes.

To the boiling mixture is added phthalic acid anhydride (126.2 g, 0.85 mol) and the reaction mixture is boiled for another 2,5 hrs.

After cooling to room temperature the mixture is filtered and the solid is washed successively with glacial acetic acid and ethanol.

The product, the potassium salt of 2-phthalimidoethanesulfonyl is dried in vacuo. It is characterized by NMR, and elementary analysis.

The above product (132 g, 0.45 mol) is suspended in 660 ml of benzene. In order to remove traces of moisture 150 ml of the benzene is distilled off. The mixture is cooled to room temperature, whereupon phosphorus pentachloride (67.5 g, 0.32 mol) is added while stirring. The mixture is then refluxed for 1 hr and a further amount (67.5 g, 0.32 mol) of phosphorus pentachloride is added. The stirring and heating is continued for another 1.5 hrs, whereupon the solvent is removed in vacuo. Another 200 ml of benzene are added and the mixture is again evaporated to dryness. The residue is mixed with 900 g of crushed ice and left overnight. The solid, 2-phthalimidoethanesulfonyl chloride, is filtered off, washed with water and dried in vacuo. The product is characterized by NMR, and has a melting point of 159°–162° C.

The above product (58.7 g, 0.215 mol) is dissolved in 400 ml of toluene. A solution of dimethylamine (32.3 ml, 0.43 mol) in 80 ml of toluene is added with cooling and stirring.

The reaction mixture is stirred at room temperature for 2 hrs, whereupon 250 ml of water are added slowly. The precipitated compound, 2-phthalimidoethylsulfonyl dimethylamide, is washed with water and dried in vacuo. The product is pure in TLC, is characterized by NMR, and has a melting point of 154°–156° C.

The above product (55 g, 0.195 mol) is suspended in 360 ml of 95% ethanol whereupon hydrazine hydrate (9.8 g, 0.195 mol) is added. The reaction mixture is boiled under reflux for 3 hrs.

The precipitated product is filtered off and the filtrate is evaporated to dryness. The residue is combined with the filtered product and the mixture is slurried in 180 ml of hot water, pH is adjusted to about 3 and the mixture left overnight in the refrigerator.

The mixture is filtered and the filtrate is evaporated to dryness. The residue, 2-aminoethylsulfonyl dimethylamide hydrochloride, is recrystallised from 240 ml of isopropanol.

The product is pure in TLC, is characterized by NMR and quantitative analysis, and has a melting point of 144°–146° C.

In essentially the same manner other compounds of the general formula (III) above are obtained from the corresponding aminoalkylsulfonic acid.

EXAMPLE 20

A mixture of phthalimide (100 g, 0.68 mol.), potassium carbonate (50 g, 0.36 mol.) and trimethylenedibromide (350 g, 1.73 mol.) is gradually heated until reaction begins. The reaction is carried out in a vessel equipped with an efficient double mantled condenser.

When a clear reaction mixture is obtained, the heating is maintained for 2 hrs whereupon excess of trimethylenedibromide is distilled off by means of steam distillation. The residue is recrystallised from 100 ml of ethanol.

The crystallised product is extracted with petroleum ether. The extract is evaporated to dryness, leaving the 3-bromopropylphthalimide (m.p. 72°–73° C.) as a white crystalline solid.

A mixture of the above product (103 g, 0.38 mol.), thiourea (29.3 g, 0.38 mol.) and 200 ml of 95% aqueous ethanol is boiled under reflux for 8 hrs.

On cooling, the S-3-phthalimidopropyl thiuronium bromide precipitates and is filtered off and washed with ethanol. Recrystallisation from water gives a pure product (m. p. 225°–227° C).

To a hot aqueous solution of the above product (50 g, 0.15 mol.) is added a solution of potassium acetate (56 g., 0.57 mol.) in 50 ml of hot water. The mixture is stirred and kept at 80° C. for 1 hr.

After cooling, the crystallised thiuronium acetate is filtered off and then suspended in a mixture of 340 ml of water and 4.5 g of concentrated hydrochloric acid. On cooling (0°–5° C.) chlorine is passed into the solution while stirring. After about 3 hrs. the 3-phthalimidopropane-1-sulfonyl chloride is filtered off and washed with water. The product is purified by dissolving it in hot benzene, filtering the solution and precipitating the product by addition of light petroleum.

The product has a m. p. of 77°–78° C. (when dried in vacuo over $H_2SO_4$).

The above product (61.9 g, 0.215 mol.) is dissolved in 400 ml of toluene. A solution of dimethylamine (32.3 ml, 0.43 mol.) in 80 ml of toluene is added with cooling and stirring.

The reaction mixture is stirred at room temperature for 2 hrs, whereupon 250 ml of water are added slowly. The precipitated compound, 3-phthalimidopropane-1-sulfonyldimethylamide is washed with water and dried in vacuo. The product is pure in TLC and is characterized by NMR.

The above product (55 g, 0.195 mol.) is suspended in 360 ml of 95% ethanol whereupon hydrazine hydrate (9.75 g, 0.195 mol.) is added. The reaction mixture is boiled under reflux for 3 hrs.

The precipitated product is filtered off and the filtrate is evaporated to dryness. The residue is combined with the filtered product and the mixture is slurried in 180 ml of hot water, pH is adjusted to about 3 and the mixture left overnight in the refrigerator.

The mixture is filtered and the filtrate is evaporated to dryness. The residue, crude 3-aminopropyl-1-sulfonyldimethylamide hydrochloride is recrystallised from 240 ml of isopropanol and dried in vacuo.

The product is pure in TLC and is characterized by NMR and quantitative analysis.

In the foregoing Examples 10–16 relating to compositions the Active Compounds are those covered by the general formula (I) above. Those Active Compounds which are disclosed in the foregoing Examples 1–8 are preferred as Active Compounds.

Also, it is to be noted that two or more Active Compounds of the invention may be used in combination in the compositions illustrated, and also if desired in combination with other pharmacologically active agents.

Various modifications and equivalents will be apparent to one skilled in the art and may be used in the compounds, compositions and methods of the present invention without departing from the spirit or scope thereof, and it is therefore to be understood that the invention is not to be limited to the specific examples and embodiments disclosed herein.

Literature references

1. Carter, Bakowski Hellman—Chemotherapy of Cancer, Wiley, 1977, p. 70–72
2. Wasserman—Cancer 36 (1975), 1258
3. Schacht—Cancer 48 (1981), 1328
4. Weiss—Cancer Treatment Reviews 8 (1981), 111
5. Schein—Cancer and Chemotherapy, vol. III, Academic Press, 1981, p. 37
6. Belt—Cancer Treatment Reports 64 (1980):12, 1235
7. Ahlgren—Cancer Treatment Reports 65 (1981), 223
8. Sandler, Karo—Functional Group Preparations, vol. 2 (1971), Academic Press, chapter 17
9. Houben-Weyl, vol. 9 (1955), 343
10. Sandler, Karo—Functional Group Preparations, vol. 2 (1971), Academic Press, chapters 10, 11 and 17
11. Martinez—J. Med. Chem. 25 (1982), 178
12. Sandler, Karo—Functional Group Preparations, vol. 2 (1971), Academic Press, chapter 6
13. McOmie—Protective Groups in Organic Chemistry, Plenum Press, 1973
14. Greene—Protective Groups in Organic Synthesis, Wiley, 1981
15. Hoyben-Weyl, vol. 15/1 (1974)
16. Cancer Chemotherapy Reports, December, 1962
17. Cancer Chemotherapy Reports, September, 1972, vol. 3 no 2
18. Sandler, Karo—Functional Group Preparations, vol. 1 (1968), Academic Press, chapter 12

19. Mead, Koepfli—J. Org. Chem. 12 (1947), 295
20. McIlwain—J. Chem. Soc. 1941, 75
21. Brynes—J. Med. Chem. 21 (1981), 45
22. Griffin, Hey—J. Chem. Soc. 1952, 3334

What we claim is:

1. Compound having the formula:

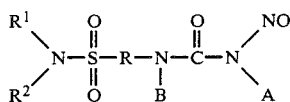

wherein
- A is lower alkyl or halolower alkyl;
- B is hydrogen, lower alkenyl; lower alkynyl; 3–6 C cycloalkyl;—R'SO$_2$NR$^3$R$^4$, or lower alkyl optionally monosubstituted with lower alkoxy or 3–6 C cycloalkyl;
- R and R' are straight or branched 2–5 C alkylene, R being optionally monosubstituted with SO$_2$NR$^3$R$^4$ or CONR$^3$R$^4$, said R and R' alkylene always containing at least two carbon atoms separating the nitrogen atom of the urea from any SO$_2$NR$^1$R$^2$ or SO$_2$NR$^3$R$^4$;
- R$^1$ and R$^2$ are the same or different and selected from hydrogen, 5–6 C cycloalkyl, lower alkoxy, phenyl, benzyl, and straight or branced 1–6 C alkyl, optionally monosubstituted with hydroxy, lower alkoxy, SO$_2$NR$^3$R$^4$, or CONR$^3$R$^4$; R$^1$ and R$^2$ may also together form a 4–5 C alkylene;
- R$^3$ and R$^4$ are the same or different and selected from hydrogen and lower alkyl, with the proviso that no more than one of R$^1$, R$^2$, R, and B may contain a sulfonamide or carboxamide moiety at the same time.

2. Compound according to claim 1, characterized in that A is chloroethyl or fluoroethyl.

3. Compound according to claim 1, characterized in that R is unsubstituted 2–5 C alkylene.

4. Compound as in any of claims 1 through 3, wherein B is hydrogen or lower alkyl.

5. Compound as in any of claims 1 through 3, wherein one of the substituents R$^1$ and R$^2$ is methyl and the other of the substituents R$^1$ and R$^2$ is lower alkyl or 2-hydroxyethyl.

6. Compound as in any of claims 1 through 3, wherein R$^1$ and R$^2$ are the same and selected from the group hydrogen, methyl, ethyl and propyl, or wherein R$^1$ and R$^2$ together are 5 C alkylene.

7. Compound as in any of the claims 1 through 3, wherein R$^1$ and R$^2$ are hydrogen or methyl.

8. Compound according to claim 1 selected from the following group:
   (a) 1-(2-chloroethyl)-3-/2-(dimethylaminosulfonyl)ethyl/-1-nitrosourea
   (b) 1-(2-chloroethyl)-3-/2-(diethylaminosulfonyl)ethyl/-1-nitrosourea
   (c) 3-/2-(aminosulfonyl)ethyl/-1-(2-chloroethyl)-1-nitrosourea
   (d) 1-(2-chloroethyl)-1-nitroso-3-/2-(1-piperidinosulfonyl)ethyl/urea
   (e) 1-(2-chloroethyl)-3-/2-(methylaminosulfonyl)ethyl/-1-nitrosourea
   (f) 1-(2-chloroethyl)-3-/2-(dipropylaminosulfonyl)ethyl/-1-nitrosourea
   (g) 1-(2-chloroethyl)-3-/2-(2-hydroxyethylaminosulfonyl)ethyl/-1-nitrosourea
   (h) 1-(2-chloroethyl)-3-/2-(N-2-hydroxyethyl-N-methyl-aminosulfonyl)ethyl/-1-nitrosourea
   (i) 1-(2-chloroethyl)-3-(2-/2-methoxyethylaminosulfonyl/ethyl)-1-nitrosourea
   (j) 1-(2-chloroethyl)-3-/2-(dimethylaminosulfonyl)ethyl/-3-methyl-1-nitrosourea
   (k) 1-(2-chloroethyl)-3-(5-/dimethylaminosulfonyl/pentyl)-1-nitrosourea
   (l) 1-(2-chloroethyl)-3-(3-/dimethylaminosulfonyl/propyl)-1-nitrosourea
   (m) 1-(2-chloroethyl)-3-(4-/dimethylaminosulfonyl/butyl)-1-nitrosourea, and
   (n) 1-(2-chloroethyl)-3-(2-/N-ethyl-N-propylaminosulfonyl/ethyl)-1-nitrosourea 9. Pharmaceutical compositions, suitable for use in the treatment of Walker carcinosarcoma 256 and L 1210 lymphatic leukemia, containing as an active ingredient one or more of the compounds of claim 1, preferably together with a pharmaceutically acceptable carrier.

10. Compound according to claim 1, wherein A is chloroethyl.

11. Compound according to claim 1, wherein R is ethylene.

12. Compound according to claim 1, wherein B is hydrogen.

* * * * *